(12) United States Patent
Galdonik et al.

(10) Patent No.: US 7,976,516 B2
(45) Date of Patent: Jul. 12, 2011

(54) MEDICAL DEVICE HAVING MECHANICALLY INTERLOCKED SEGMENTS

(75) Inventors: Jason A. Galdonik, Hanover, MN (US);
James Pokorney, Northfield, MN (US);
Matthew F. Ogle, Oronoco, MN (US)

(73) Assignee: Lumen Biomedical, Inc., Maple Grove, MN (US)

( * ) Notice: Subject to any disclaimer, the term of this patent is extended or adjusted under 35 U.S.C. 154(b) by 912 days.

(21) Appl. No.: 11/157,476

(22) Filed: Jun. 21, 2005

(65) Prior Publication Data
US 2006/0006649 A1    Jan. 12, 2006

Related U.S. Application Data

(60) Provisional application No. 60/583,222, filed on Jun. 25, 2004.

(51) Int. Cl.
*A61M 5/00* (2006.01)
(52) U.S. Cl. ................................................ 604/264
(58) Field of Classification Search .................. 604/264, 604/265
See application file for complete search history.

(56) References Cited

U.S. PATENT DOCUMENTS

| 4,610,662 A | 9/1986 | Weikl et al. |
| 4,723,549 A | 2/1988 | Wholey et al. |
| 4,728,319 A | 3/1988 | Masch |
| 4,784,636 A | 11/1988 | Rydell |
| 4,790,812 A | 12/1988 | Hawkins, Jr. et al. |
| 4,794,928 A | 1/1989 | Kletschka |
| 4,873,978 A | 10/1989 | Ginsburg |
| 4,883,460 A | 11/1989 | Zanetti |
| 4,887,613 A | 12/1989 | Farr et al. |
| 4,994,067 A | 2/1991 | Summers |
| 5,011,488 A | 4/1991 | Ginsburg |
| 5,011,490 A | 4/1991 | Fischell et al. |
| 5,053,008 A | 10/1991 | Bajaj |

(Continued)

FOREIGN PATENT DOCUMENTS
WO    WO 95/05209    2/1995
(Continued)

OTHER PUBLICATIONS

Feldman, "Transcatheter Aspiration of a Thrombus in an Aortocoronary Saphenous Vein Graft," Am. J. Cardiol. Aug. 1, 1987, 60(4), 379-380.

(Continued)

*Primary Examiner* — Nicholas D Lucchesi
*Assistant Examiner* — Victoria P Campbell
(74) *Attorney, Agent, or Firm* — Dardi & Herbert, PLLC; Peter S. Dardi; Mengmeng Fahrni (57) ABSTRACT

A biocompatible medical device having a segmented element including a first segment having a first shaped interface and a second segment having a second shaped interface configured to operably couple the first shaped interface. When the first shaped interface is engaging the second shaped interface to form a joined segmented element, the first segment and the second segment cannot be decoupled by movement along an axis through the element. The medical device further includes a locking element configured to engage the joined segmented element with a sliding motion to prevent decoupling of the first segment with respect to the second segment by preventing significant relative movement of the segments with a component of the movement perpendicular to the axis.

23 Claims, 8 Drawing Sheets

U.S. PATENT DOCUMENTS

| | | |
|---|---|---|
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,163,906 A | 11/1992 | Ahmadi |
| 5,211,651 A | 5/1993 | Reger et al. |
| 5,549,626 A | 8/1996 | Miller et al. |
| 5,599,307 A | 2/1997 | Bacher et al. |
| 5,766,191 A | 6/1998 | Trerotola |
| 5,810,874 A | 9/1998 | Lefebvre |
| 5,814,064 A | 9/1998 | Daniel et al. |
| 5,836,868 A | 11/1998 | Ressemann et al. |
| 5,843,051 A | 12/1998 | Adams et al. |
| 5,897,567 A | 4/1999 | Ressemann et al. |
| 5,911,725 A | 6/1999 | Boury |
| 5,911,734 A | 6/1999 | Tsugita et al. |
| 5,938,645 A | 8/1999 | Gordon |
| 5,941,869 A | 8/1999 | Patterson et al. |
| 5,997,557 A | 12/1999 | Barbut et al. |
| 6,010,522 A | 1/2000 | Barbut et al. |
| 6,022,336 A | 2/2000 | Zadno-Azizi |
| 6,066,149 A | 5/2000 | Samson et al. |
| 6,135,991 A | 10/2000 | Muni et al. |
| 6,142,987 A | 11/2000 | Tsugita |
| 6,159,195 A | 12/2000 | Ha et al. |
| 6,165,183 A | 12/2000 | Kuehn et al. |
| 6,168,579 B1 | 1/2001 | Tsugita |
| 6,203,561 B1 | 3/2001 | Ramee et al. |
| 6,206,868 B1 | 3/2001 | Pariodi |
| 6,258,115 B1 | 7/2001 | Dubrul |
| 6,270,477 B1 | 8/2001 | Bagaoison et al. |
| 6,361,545 B1 | 3/2002 | Macoviak et al. |
| 6,454,741 B1 | 9/2002 | Muni et al. |
| 6,485,500 B1 | 11/2002 | Kokish |
| 6,569,148 B2 | 5/2003 | Bagaoisan et al. |
| 6,596,011 B2 | 7/2003 | Johnson et al. |
| 6,620,148 B1 | 9/2003 | Tsugita |
| 6,706,055 B2 | 3/2004 | Douk et al. |
| 6,805,692 B2 | 10/2004 | Muni et al. |
| 6,911,036 B2 | 6/2005 | Douk et al. |
| 2002/0035347 A1 | 3/2002 | Bagaoisan |
| 2002/0095174 A1* | 7/2002 | Tsugita et al. ............... 606/200 |
| 2003/0023263 A1 | 1/2003 | Krolik et al. |
| 2004/0006365 A1 | 1/2004 | Brady et al. |
| 2004/0116831 A1 | 6/2004 | Vrba |
| 2004/0220611 A1 | 11/2004 | Ogle |
| 2004/0254450 A1* | 12/2004 | Griffin et al. ............... 600/411 |
| 2005/0021152 A1 | 1/2005 | Ogle et al. |
| 2005/0085847 A1 | 4/2005 | Galdonik et al. |
| 2005/0209631 A1 | 9/2005 | Galdonik et al. |

FOREIGN PATENT DOCUMENTS

| | | |
|---|---|---|
| WO | WO 98/38930 | 9/1998 |
| WO | WO 02/085092 | 10/2002 |
| WO | WO 2005/086796 | 9/2005 |

OTHER PUBLICATIONS

Nakagawa et al., "A Retrievable Nitinol Vena Cava Filter: Experimental and Initial Clinical Results," J. of Vascular and Interventional radiology, May-Jun. 1994; 5:507-512.

Galdonik, U.S. Appl. No. 11/072,011, filed Mar. 4, 2005, entitled "Steerable Device Having a Corewire Within a Tube and Combination with a Functional Medical Component."

* cited by examiner

MEDICAL DEVICE HAVING MECHANICALLY INTERLOCKED SEGMENTS

CROSS REFERENCE TO RELATED APPLICATION

This application claims priority to U.S. Provisional Application No. 60/583,222, to Galdonik et al., filed Jun. 25, 2004, entitled "Medical Articles Having Mechanically Interlocked Materials," incorporated herein by reference.

FIELD OF THE INVENTION

The present invention relates generally to a medical device for less invasive medical procedures. More particularly, the invention relates to a medical device having mechanically interlocked segments comprisable of different materials to provide the medical device with flexibility and manipulability.

BACKGROUND OF THE INVENTION

A variety of less invasive procedures can be performed on a patient to reach selected locations within the patient's body. These procedures can be used, for example, for entry into the abdominal cavity or urinary track, or for reaching the patient's genital organs. Many of these less invasive procedures are also performed within a patient's cardiovascular system. For any of these procedures, guidewires or other medical device structures are often used to snake through the vascular system and position the device at a desired location within the patient. If a guidewire has been positioned within the patient, a stent, catheter, balloon, or other medical device can then be positioned within the system by sliding them over the guidewire to a desired location.

Generally, when positioning the guidewire within the patient's body, the wire traverses along a pathway, such as vessels of the cardiovascular system. These pathways often include many obstacles, such as curves, bends, and branches, which can make positioning considerably more complicated than following a clear path. To navigate along the curves and branches, guidewires and catheters are often made of flexible materials, such as spring stainless steel or shape memory alloys, which enable flexing of the components with the curves and branches. However, using materials with too much flexibility can inhibit the control and steerability of the guidewire and overall manipulability of medical device components.

SUMMARY OF THE INVENTION

In a first aspect, the invention pertains to a biocompatible medical device having a segmented element including a first segment having a first shaped interface and a second segment having a second shaped interface configured to operably couple the first shaped interface. When the first shaped interface is engaging the second shaped interface to form a joined segmented element, the first segment and the second segment cannot be decoupled by movement along an axis through the element. The device further includes a locking element configured to engage the joined segmented element with a sliding motion to prevent decoupling of the first segment with respect to the second segment by preventing significant relative movement of the segments with a component of the movement perpendicular to the axis.

In further aspects, the invention pertains to a method for using a biocompatible medical device including inserting into the patient through an incision in the patient's thigh, arm, or neck and directing the device through appropriate vessels to a desired location within a patient. The invention further pertains to an embolism protection device connected to a joined segmented element of the medical device and deploying the embolism protection structure to a vessel and expanding the embolism protection structure within the vessel.

Moreover, the invention pertains to a method of using a biocompatible medical device having a locking element and a segmented element including first and second coupled segments operably inseparable along an axis. The method includes sidably engaging the locking element with the segmented element to prevent decoupling of the segments by preventing relative movement of the segments with a component of the movement perpendicular to the axis.

DETAILED DESCRIPTION OF THE PRESENT INVENTION

The medical devices of the various embodiments having interlocking segments described herein generally comprises an elongated element with the segments that interlock and a locking element. The elongated element can be, for example, a corewire or a tube, and comprises a first segment with a first shaped or contoured interface and a second segment having a second shaped or contoured interface configured to operably mate or couple with the first shaped locking interface. The first and second segments can be operably coupled to form a mechanical locking interface. The mechanical interface generally enables the segments to be effectively fixed with respect to one another along a major axis of the elongated element and to disengage only through motions of the segments generally perpendicular to the major axis. In some embodiments, the mechanical interface can comprise interlocking contours that are designed as cut outs that fit together to form a smooth profile along the elongated structure. Specifically, in some embodiments the mechanical interface can comprise a first interface formed into the first segment that can couple with a mated structure or second interface formed into the second segment such that the corresponding elements fit together, for example, like pieces of a jug saw puzzle to form a structure that is essentially an elongated structure with a smooth effectively continuous surface(s).

The locking element can be, for example, a corewire or a tube, and can slidably engage the elongated element in a sliding motion parallel to the major axis of the elongated element. The locking element can be positioned with respect to the elongated element to restrict transverse motion at the mechanical locking interface to prevent the motion of the two interlocked sections in the direction generally perpendicular to the major axis of the elongated element. Thus, the locking element can effectively fix the mechanically interlocked sections with respect to each other. A joining composition, such as a solder, an adhesive or other polymer coating, can be used to supplement the mechanical bonding.

The mechanical locking can effectively bond together two elements without bonding the materials directly together. The distinct elements can comprise the same materials as each other, or the elements can be composed of different materials from each other. Thus, the mechanical interface can be used, for example, to join two different materials or to join elements for later separation. In some embodiments, the mechanical interface can enable components of medical devices to be produced having expensive materials such as, e.g., nickel titanium alloy NITINOL®, employed in desired locations of the device, while other portions of the device can be produced using relatively lower costs materials such as, for example, biocompatible stainless steels.

Similarly, the mechanical interface facilitates the production of medical devices that can have different mechanical properties, such as flexibility, rigidity, kink resistance, shape memory and the like, at desired locations along the length of the elongated element. This type of coupling can be particularly useful with materials or alloys that are difficult to weld, solder, or bond using non-mechanical approaches. Moreover, the joined materials may not have a desired degree of mechanical strength following welding or the like, and adhesives alone may not provide suitable mechanical strength required at the junctures of wire segments.

In one embodiment, the medical device comprises an integrated guiding structure with a corewire and a tube, such as a hypotube or polytube. The tube can have a bore defined therein extending along the major axis of the tube. The corewire can be selectively disposed within the bore such that the wire is slidable within at least a portion of the tube. In various embodiments, the surface of the corewire, the inner surface of the tube, and/or the outer surface of the tube can be coated with a friction reducing agent. Suitable friction reducing agents include, for example, suitable polymers, such as polytetrafluoroethylene, i.e., TEFLON®. The coating of the corewire or tube can facilitate relative longitudinal motion of the wire relative to the tube.

With respect to mechanical bonding of a corewire, once the mechanically coupled segments of the corewire are inserted into a corresponding tube, uncoupling of the first segment and the second segment can be inhibited, as the distance the first segment can move away from the second segment is fixed by the inner wall of the tube. If the corewire with joined segments is subsequently removed from the tube, the segments can then be separated. Additionally in some embodiments, the segments can be fixed through welding or with a joining composition, such as a polymer, adhesive or solder. Approaches to fix the segments may be used to further strengthen the mechanical interface and prevent the first segment from uncoupling from the second segment. If a joining composition or welding is used, the joining composition would hold the segments together following removal of the corewire from the tube. Furthermore, in some embodiments, the elongated element and the locking element may incorporate structural features that restrict or eliminate relative longitudinal motion such that the elongated element and the locking element remain associated such that the first segment and second segment remain interlocked unless the structure is damaged to free the elements.

In other embodiments, the tube can comprise a first segment connected to a second segment via a mechanical interface, which permits the tube to be composed of two or more materials. Transverse motion can join the two segments of the tube together at a mechanical interface. The insertion of a corewire into the tube prevents the transverse motion of the tube segments to lock the tube segments together. If the corewire is subsequently removed, the tube segments can be separated assuming that the elements are designed to provide for their subsequent separation. Again, a joining composition or welding can be used to supplement the mechanical interlocking of the tube segments as well as to hold the segments together with the removal of the corewire.

In further embodiments, a tube and a corresponding corewire both can comprise a first segment coupled to a second segment via a mechanical interface as described above. In these embodiments, the tube and the corewire both can be described as the elongated structure, and the other element functions as the locking element. Because of the respective mechanical interfaces, each of the tube and the corewire can comprise two or more segments, or sections, having different compositions. This can enable producing a medical device that has desired physical properties such as, for example, flexibility, rigidity, kink resistance, shape memory, and strength at desired, different locations along the length of the medical device. With respect to other alternative designs, both the elongated element and the locking element can be tubular with one element inserting within the other element. One or both of these nested tubular elements can have interlocking mechanical interfaces with the other element functioning as the locking element. Similarly, any other elongated structure within a medical device can have joined segments using a locking structure to be placed over the element.

In general, a range of medical devices can incorporate interlocking segments as described here. For example, various catheters, cannulas, imaging devices, angioplasty balloon devices, stent delivery devices and the like can comprise components with interlocking segments. Suitable medical devices include, for example, medical devices that are placed within a patient, such as prostheses, or percutaneous devices that are inserted for various lengths of time from outside the body into the body, such as catheter. Any of these medical devices can effectively take advantage of the mechanical joining described herein.

In embodiments of particular interest, the medical devices can comprise an integrated guiding structure. An integrated guiding structure can comprise a tube with a lumen and a corewire that fits within the lumen of the tube. It may be desirable to provide for at least some relative longitudinal movement of the corewire relative to the tube. Furthermore, it can also be desirable to provide torque coupling between the corewire and the tube such that torque applied to one of the elements at a proximal end can be more effectively transferred to a distal end. A torque coupler may restrict or eliminate relative longitudinal motion of the corewire relative to the tube. An integrated guide structure with a torque coupler is described further in copending U.S. patent applications Ser. No. 10/979,439 to Galdonik et al., and Ser. No. 11/072,001 to Galdonik et al., both entitled "Steerable Device Having a Corewire Within a Tube and Combination with a Functional Medical Component," both of which are incorporated herein by reference.

An integrated guiding structure can be used for the delivery of appropriate medical treatment devices. For example, any medical device that can be delivered over a conventional guidewire can be delivered over an integrated guide structure, such as an angioplasty balloon and/or a stent delivery device. In addition, a single integrated device can comprise a tube, corewire, and a functional medical component, such as an actuatable medical structure, which can be integrated into the guiding device structure, as described further in copending U.S. patent application Ser. No. 11/072,001 to Galdonik et al., entitled "Steerable Device Having a Corewire Within a Tube and a Combination with a Functional Medical Component," which is incorporated herein by reference. In some embodiments, the tube can have approximately the outer dimensions of a standard guidewire. If the tube has the outer dimensions of a standard guidewire, standard interventional devices such as balloons, stents, and pacing leads can be delivered over the tube.

The functional medical structure can be located, for example, at or near the distal end of the integrated guiding device. In these embodiments, the longitudinal movement of the corewire with respect to the small tube enables the actuating features of a functional medical component coupled at the distal end of the device. Additional functionality can result from the ability to provide distant communication from the distal end to the proximal end through the relative longitudinal motion of the corewire and the tube.

It can be desirable to interface the functional medical structures with both the corewire and the tube. By interfacing the functional medical structure to the corewire and the tube, the longitudinal motion of the corewire with respect to the tube can be used to send a signal to the functional medical structure from outside of the patient's body. Specifically, the longitudinal motion of the corewire and the tube can be used to actuate or de-actuate the functional medical structure. Suitable functional medical structures include, for example, embolism protection structures. The use of such structure for the deployment of an embolism protection device and aspiration catheter is described further in copending U.S. patent applications Ser. No. 10/854,920 to Galdonik et al., entitled "Emboli Filter Export System," and Ser. No. 11/072,001 to Galdonik et al., entitled "Steerable Device Having a Corewire Within a Tube and a Combination with a Functional Medical Component," both of which are incorporated herein by reference.

The medical devices described herein can be used effectively to guide the corewire and associated medical devices through intricate passageways within the body. Specifically, devices can be guided into coronary arteries as well as along similar highly branched and curved vessels. The integrated guiding devices described herein can provide improved performance for a range of medical procedures involving less invasive intervention.

The devices described herein also provide for very small diameter components with excellent maneuverability while maintaining desirable degrees of freedom. The devices used with integral medical structures and/or with associated medical devices delivered over the tube can be positioned precisely within the body with less effort while providing desired functionality by the ability in appropriate embodiments to longitudinally move the corewire and the tube relative to each other. Thus, functionality can be maintained without sacrificing the ease of steering of the device to a selected location within a patient's body.

Structure of the Medical Device

In general, a range of medical devices can advantageously take advantage of the mechanical segment joining described herein. The different embodiments have in common an elongated structure with two segments to be joined and a locking structure that slides with respect to the longitudinal direction of the elongated structure to mechanically lock the joined segments. Several specific embodiments are described in the following. In embodiments of particular interest, the medical device is an integrated guide structure, which is described further below.

The length and other dimensions of the elongated element can be selected for the particular application. While the segmented element is referred to as an elongated element, the element may or may not be elongated to a large degree, although the elongated feature is conducive to sliding engagement with the locking element. In some embodiments, the elongated element can have an aspect ratio of length to average thickness of at least about 1.5, in further embodiments at least about 2 and in other embodiments the aspect ratio may be relatively large, such as for use as in an integrated guide structure. For example, for a less invasive tool for intervention in the aorta, the elongated element generally can have a length from about 190 cm (63 inches) to about 300 cm (106 inches).

For an integrated guide structure, the cross section of the tube can be characterized by an inner diameter and an outer diameter. The inner diameter general ranges from about 0.001 inches to about 0.01 inches, in further embodiment from about 0.003 inches to about 0.008 inches and in additional embodiments from about 0.005 inches to about 0.007 inches. The outer diameter generally ranges from about 0.04 inches to about 0.009 inches, in further embodiments from about 0.03 inches to about 0.010 inches, in additional embodiments from about 0.02 inches to about 0.011 inches and in other embodiments from about 0.015 inches to about 0.013 inches, with standard guidewire outer diameters being about 0.014 inches. The corewire has a diameter slightly less than the inner diameter of the tube by about 0.002 inches to about 0.003 inches. A person of ordinary skill in the art will recognize that additional ranges within the explicit ranges for the diameters are contemplated and are within the present disclosure.

While in some embodiments of an integrated guide structure the corewire and tube have especially thin cross sections, in other embodiments the corewire can have conventional thicknesses of a corewire and the tube can have conventional dimensions of a catheter. However, for embodiments in which the corewire and tube have particularly thin cross sections, due to the extremely thin nature of the corewire, the wire can twist such that torque cannot be efficiently transferred from the distal end of the corewire to the proximal end of the corewire without the presence of the torque coupler. For any of the embodiments, to facilitate transfer of torque from the distal end to the proximal end, the corewire and tube can be coupled together to provide to torque transmittal, i.e., rotational communication, from the tube to the corewire. It can be advantageous to introduce torque coupling between tube and the guidewire as described further in copending U.S. patent application Ser. No. 10/979,439 to Pokorney et al., entitled "Steerable Device Having a Corewire Within a Tube and Combination with a Functional Medical Component," incorporated herein by reference. Such a torque coupling can enable the tube and corewire to be manipulated in relative conjunction with each other. In several embodiments herein in which one of the elements is tubular, it is recognized that a tubular element can have a gap or slit as long as the function of the tube is not impaired, to achieve a substantially similar function.

In various embodiments of an integrated guide structure, the corewire has a length such that it can extend past the distal end of the tube while extending also from the proximal end of the tube. Generally, the corewire extends from the proximal end of the tube to provide for independent manipulation of the corewire relative to the tube, especially for longitudinal movement and from the distal end for attachment to a medical device, such as grippers or an embolism protection device.

The outside of tube or guidewire or a portion thereof, such as a portion at or near the distal end, can have surface capillary fibers associated with the surface. The attachment of the surface capillary fibers generally depends on the material of the surface. For example, covalent bonding and/or adhesives can be used for the attachment. Surface capillary fibers have contoured surfaces with one or more surface capillaries along the length of the fiber or a portion thereof. The surface capillary fibers can moderate the character of fluid flow along the surface, such as reducing turbulence and can be used to effectively deliver bioactive agents in a controlled fashion. The use of surface capillary fibers in medical devices generally and catheters and associated articles is described further in copending U.S. patent application Ser. No. 10/781,503 to Ogle et al., filed on Feb. 18, 2004, entitled "Medical Article Incorporating Surface Capillary Fiber," incorporated herein by reference.

As described herein, a method of connecting various metals and/or metal alloys to form joined structures includes employing a mechanical interface that locks together two adjacent segments combined with a locking element that can go within or around the mechanical interface while maintaining a desired low profile or small cross section.

Figure 1:
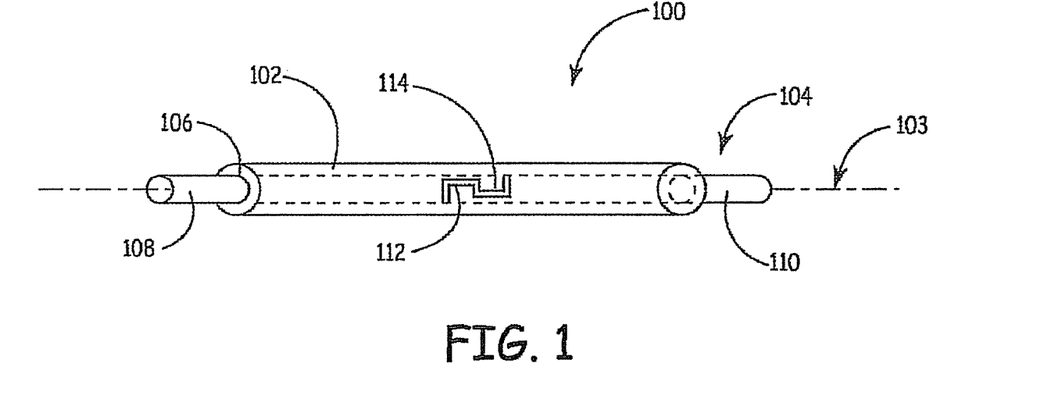
FIG. 1 is a perspective view of a medical device of a first embodiment of a medical device with interlocking segments with the portion of an elongated segmented element depicted in phantom lines located within a locking element.
Figure 2:
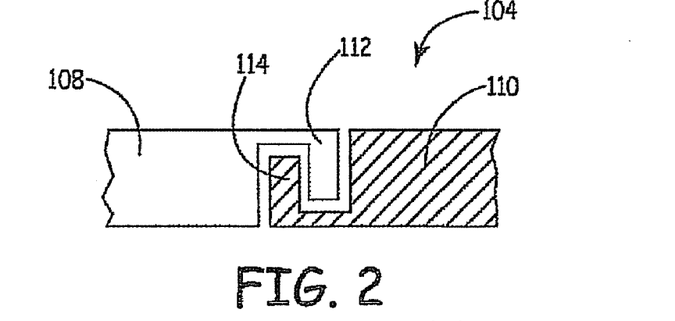
FIG. 2 is a fragmentary side view of the elongated segmented element of FIG. 1 depicting a first segment coupled to a second segment via a mechanical interface.
Figure 3:
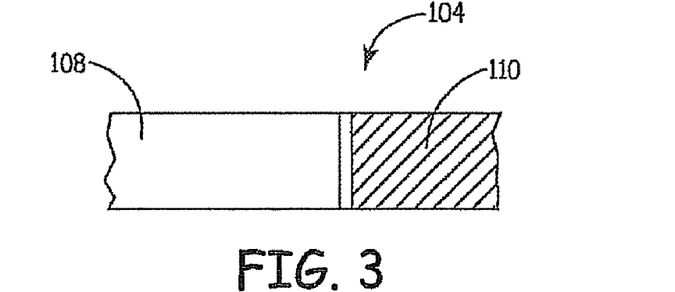
FIG. 3 is a fragmentary top view of the elongated segmented element of FIG. 1.
Figure 4:
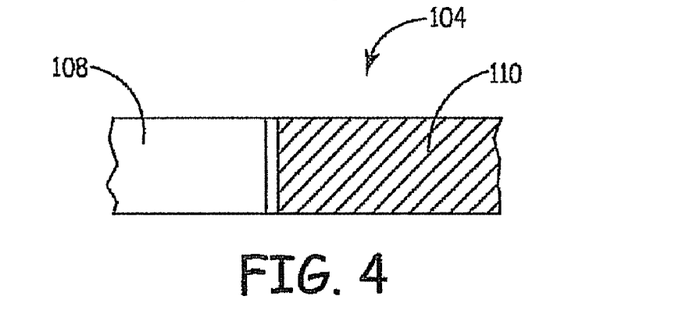
FIG. 4 is a fragmentary bottom view of the elongated element of FIG. 1.

In some embodiments, a medical device comprises a tube and a corewire extending into the interior of tube. A first embodiment is depicted in FIGS. 1-4. In this embodiment, segments of a corewire are mechanically bonded using an approach described herein. Referring to FIG. 1, medical device 100 is depicted comprising a tube 102 and a corewire 104 extending into the interior of tube 102. Generally, tube 102 has a major axis 103 along an elongated dimension of the tube relative to a minor axis lying in a minor plane, and a bore 106 that runs substantially parallel to the major axis. As depicted in FIG. 1, the corewire 104 can be selectively and slidably positioned within bore 106. Corewire 104 is elongated also along axis 103.

Referring to FIGS. 1-4, corewire 104 can comprise first segment 108 mechanically coupled to second segment 110. In some embodiments, first segment 108 can comprise key portion 112 which can mate with corresponding lock portion 114 formed into second segment 110 to mechanically mate first segment 108 to second segment 110. Although FIG. 1 depicts an embodiment where the key structure and corresponding lock structure comprise a groove and protrusion structure, one of ordinary skill in the art will recognize that any set of corresponding shapes which permit a first segment to be mechanically mated to a second segment can be employed in the devices of the present disclosure.

The shape, size and other features of the key and lock portions 112, 114 can be selected based on particular design considerations by a person of ordinary skill with the constraint that the key portions 112 mate with the lock portions 114. While the two interfacing surfaces can be cut outs relative to each other, in other embodiments there can be gaps in the interface as long as the interfacing surfaces hold the segments in place. Similarly, the number of key and lock portions 112, 114 can be one, two, three, four or more as appropriate. The key and lock portions 112, 114 can be formed along with the respective tube and corewire, for example, by machining, for example, by molding or adhering the structures.

In various embodiments, first segment 108 can be composed of different material than second segment 110, and therefore the mechanical interface permits corewire 104 to have different materials located in desired positions along the length of corewire 104. In other words, the mechanical interface facilitates providing corewires that can have different materials, with desired physical properties, positioned in selected locations along the length of the corewire. In further embodiments, corewire 104 can comprise a plurality of segments, wherein each segment is mechanically mated with an adjacent segment by a key structure system.

When the corewire 104 is selectively positioned within bore 106, the bore prevents the key and lock portions 112, 114 from significant relative movement of the segments with a component of the movement perpendicular to the axis, thus effectively locking the mechanical interface 112. As used in the present application, significant relative movement means movement more than nominal movement of interlocked segments, such as movement sufficient to decouple any segments coupled at a mechanical interface. When the corewire 104 is selectively removed from the bore 106, the key and lock portions 112, 114 can be displaced in a direction along the minor plane, thus allowing the key and lock portions 112, 114 to be disengaged.

Figure 5:
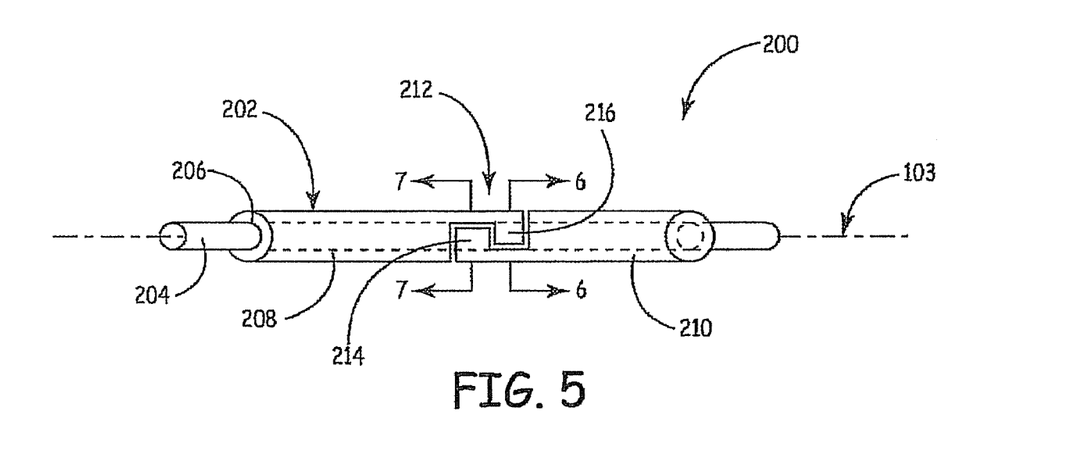
FIG. 5 is a side view of a medical device of a second embodiment of a medical device with interlocking segments with the portion of a locking element located within the elongated element depicted in phantom lines.
Figure 6:
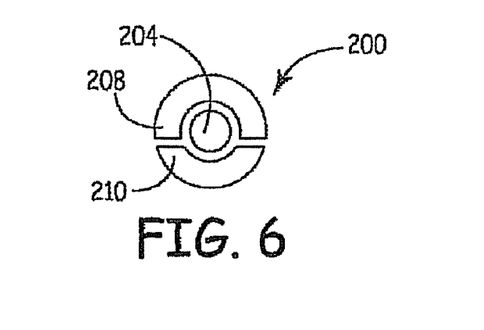
FIG. 6 is a cross-sectional view of the medical device of FIG. 5, the cross-section taken along line 6-6 of FIG. 5.
Figure 7:
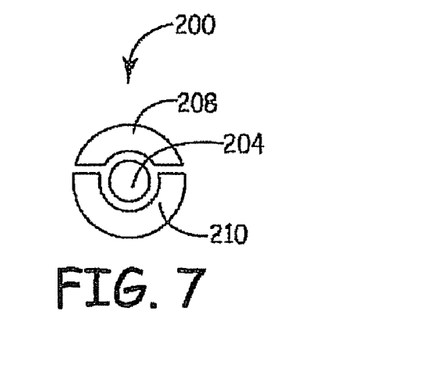
FIG. 7 is a cross-sectional view of the medical device of FIG. 5, the cross-section taken along line 7-7 of FIG. 5.

A second embodiment is depicted in FIGS. 5-7. Referring to FIG. 5, a medical device 200 is depicted comprising a tube 202 and corewire 204 extending into the interior of tube 202. As depicted in FIG. 5, tube 202 can comprise an elongated major axis 203 relative to orthogonal minor axes and a bore 206 extending through the tube running substantially parallel to the major axis. In some embodiments, corewire 204 can have an outer diameter that is slightly smaller than the inner diameter of bore 206 such that corewire 204 can be introduced into bore 206 of tube 202. In some embodiments, tube 202 can comprise first segment 208 coupled to second segment 210 by mechanical interface 212. As depicted in FIG. 5, mechanical interface 212 can comprise key structure 214 and corresponding lock structure 216, which can couple first segment 202 to second segment 204. FIGS. 6 and 7 depict cross sectional views of mechanical interface 212 taken along lines 6-6 and 7-7, respectively, of FIG. 5.

In various embodiments, first segment 208 can be composed of a different material than second segment 210, and thus mechanical interface 212 can facilitate the formation of tubes comprising multiple materials. Moreover, mechanical interface 212 can facilitate tube designs comprising different materials, having desired physical properties such as flexibility, rigidity and the like, at desired locations along the length of the tube. For example, first segment 202 can be composed of a rigid material, while second segment 204 can be composed of a flexible material. Additionally, once key structure 214 has engaged corresponding key structure 216 to mate first segment 208 to second segment 210, corewire 204 can be inserted within bore 206, which can prevent key structure 214 from uncoupling from corresponding key structure 216.

When the corewire 204 is selectively positioned within bore 206, the bore prevents the key structure 214 and corresponding lock structure 216 from moving in a direction along the minor plane, thus effectively locking the mechanical interface 212. When the corewire 204 is selectively removed from the bore 206, the key structure 214 and corresponding lock structure 216 can be displaced in a direction along the minor plane, thus allowing the key structure 214 and corresponding lock structure 216 to be disengaged.

Figure 8:
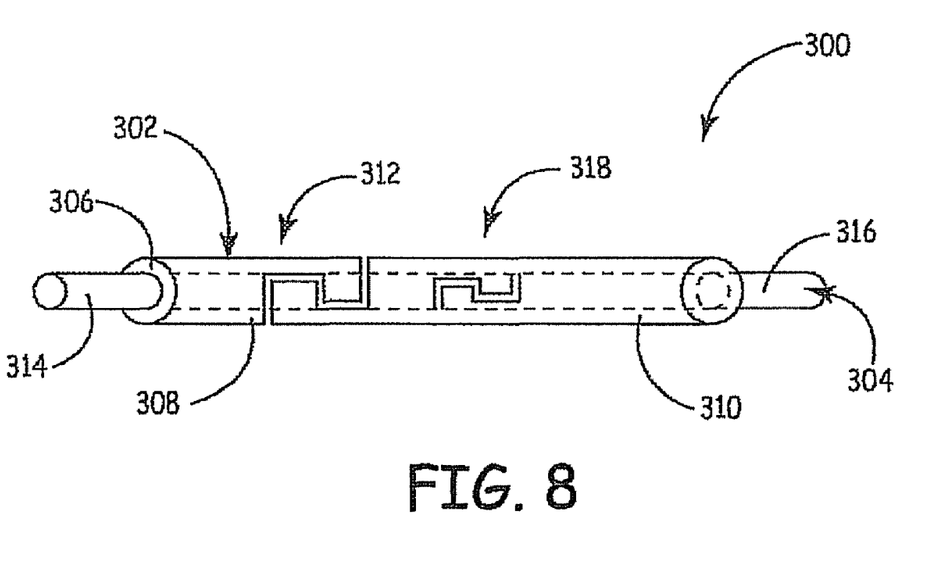
FIG. 8 is a side view of a medical device of a third embodiment of a medical device with interlocking segments with the portion of an elongated core element located within a segmented tubular element depicted in phantom lines, wherein both the elongated and locking elements comprise a first segment coupled to a second segment with a mechanical interface.

In further embodiments, both the tube and the corewire can comprise a first segment and a second segment coupled together by a mechanical interface. Referring to FIG. 8, a medical device 300 is depicted comprising tube 302 and corewire 304 extending into the interior of tube 302 through bore 306. As depicted in FIG. 8, tube 302 can comprise first segment 308 coupled to second segment 310 by mechanical interface 312, while corewire 304 can comprise first segment 314 coupled to second segment 316 by mechanical interface 318.

When the corewire 304 is selectively positioned within bore 306, the bore prevents the mechanical interfaces 312, 318 from moving in a direction along the minor plane, thus effectively locking the mechanical interfaces 312, 318. When the corewire 304 is selectively removed from the bore 306, the mechanical interfaces 312, 318 can be displaced in a direction along the minor plane, thus allowing the mechanical interfaces 312, 318 to be disengaged.

Figures 9, 9A:
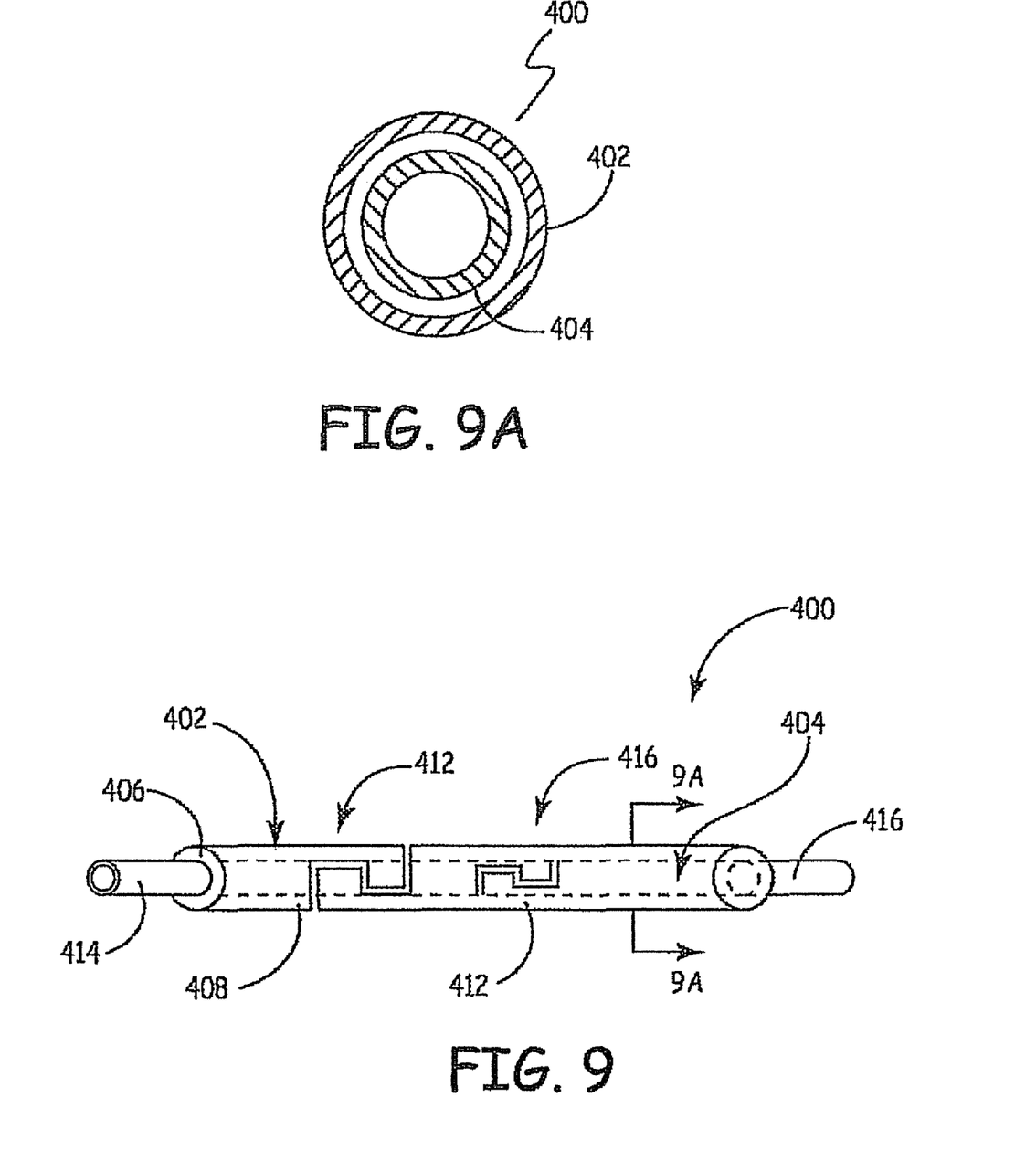
FIG. 9 is a side view of a medical device of a fourth embodiment of a medical device with interlocking segments with a portion of an segmented inner tubular element located within a segmented outer tubular element depicted in phantom lines, wherein both the elongated and locking elements comprise a first segment coupled to a second segment with a mechanical interface.
FIG. 9A is a cross-sectional view of the medical device of FIG. 9 taken along line A-A of FIG. 9.

In another embodiment, as depicted in FIGS. 9 and 9A, the medical device 400 comprises a first tube 402 and a second tube 404. Both the first and second tubes 402, 404 can comprise a first segment and a second segment coupled together by a mechanical interface, although in other embodiments only the outer tube or only the inner tube may be segmented. Referring to FIGS. 9 and 9A, a medical device 400 is depicted comprising a first tube 402 and second tube 404 extending into the interior of first tube 402 through bore 406. As depicted in FIG. 9, first tube 402 can comprise first segment 408 coupled to second segment 410 by mechanical interface 412, while second tube 404 can comprise first segment 414 coupled to second segment 416 by mechanical interface 418.

When the second tube 404 is selectively positioned within bore 406, the bore 406 prevents the mechanical interfaces 412, 418 from moving in a direction along the minor plane, thus effectively locking the mechanical interfaces 412, 418. When the second tube 404 is selectively removed from the bore 406, the mechanical interfaces 412, 418 can be displaced in a direction along the minor plane, thus allowing the mechanical interfaces 412, 418 to be disengaged.

In various embodiments, the elongated element, such as the corewire or the tube, can be fixed to hold the segments together. To fix the segments, the elongated element can be welded or covered with a joining composition, such as a solder, polymer layer and/or adhesive, to increase the joint strength of the mechanical interface. Welding can be performed, for example, with thermal welding, laser welding or the like. Also, for example, the polymer layer can be a shrink-wrap material. Examples include, for example, polytetrafluoroethylene (PTFE), fluorinated ethylene propylene films (FEP), poly(ethylene terephthalate) (PET), polyvinylchloride (PVC) and polyolefins. In particular, PET is desirable due to a high tensile strength and the corresponding ability to form small wall thicknesses. Additionally, coating the corewire with a polymer can also aid in handling the elongated element during assembly of the medical device.

Figure 10:
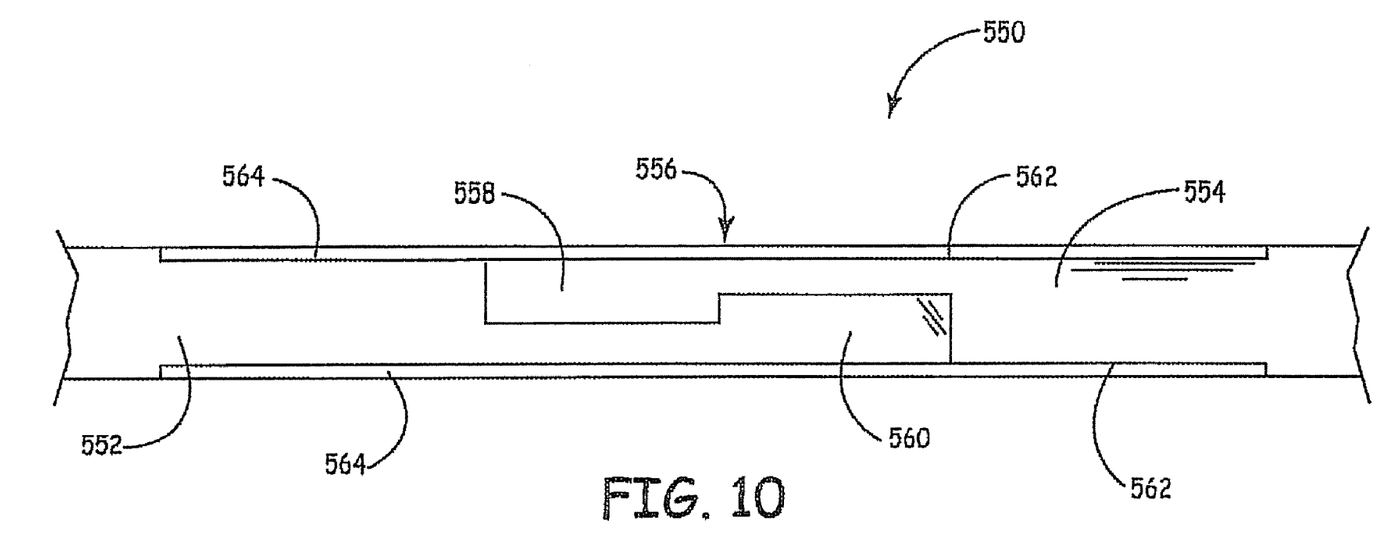
FIG. 10 is a side view of a connected element of a medical device of a fifth embodiment of a medical device with interlocking segments having a narrowed portion and polymer coating.

In other embodiments, to enable the resulting structure to have a relatively constant diameter surface, the joining composition, such as a solder, polymer coating and/or adhesive, can be placed within a recess, such as a narrowed diameter section, with a depth approximating the thickness of the polymer coating. Referring to FIG. 10, an elongated structure 550 is depicted having first segment 552 connected to second segment 554 by mechanical interface 556. As depicted in FIG. 10, mechanical interface 556 can comprise key structure 558 and corresponding lock structure 560. In embodiments where a polymer coating 564 is applied to elongated structure 550, recess 562 can be provided along the length, or major axis, of corewire 550 such that the polymer coated segment of corewire 550 has substantially the same outer diameter as the outer diameter of the segments that do not have a polymer coating. Thus, recess 562 facilitates coating portions of the corewire with a polymer without substantially increasing the outer diameter of the corewire. The polymer coating can be, for example, polyamides (Nylon), polyurethane, polyester, polyether-block-amide (PEBA, such as PEBAX®) or combinations thereof. An adhesive, such as a polyurethane oligo mixture, a polyurethane adhesive, an epoxy or a combination thereof can also be used to coat the corewire and/or tube. Biocompatible solders for dental and medical applications are commercially available.

Figure 11:
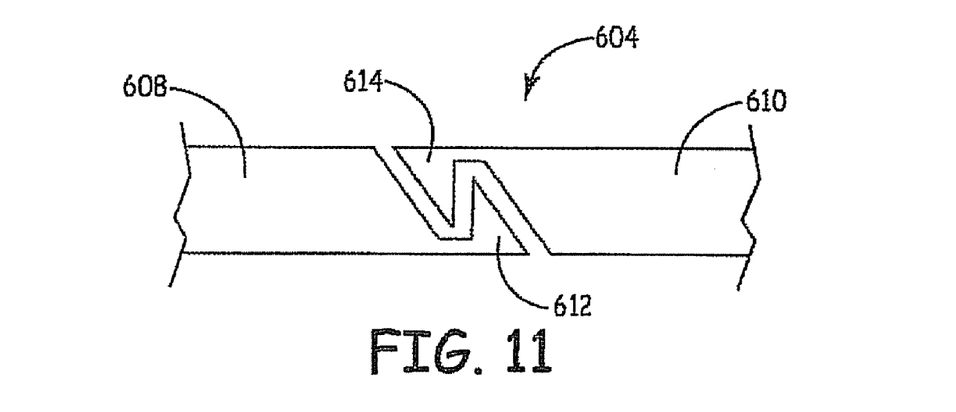
FIG. 11 is a fragmentary side view of an elongated element of a sixth embodiment of a medical device with interlocking segments depicting a first segment coupled to a second segment via a jagged mechanical interface.
Figure 12:
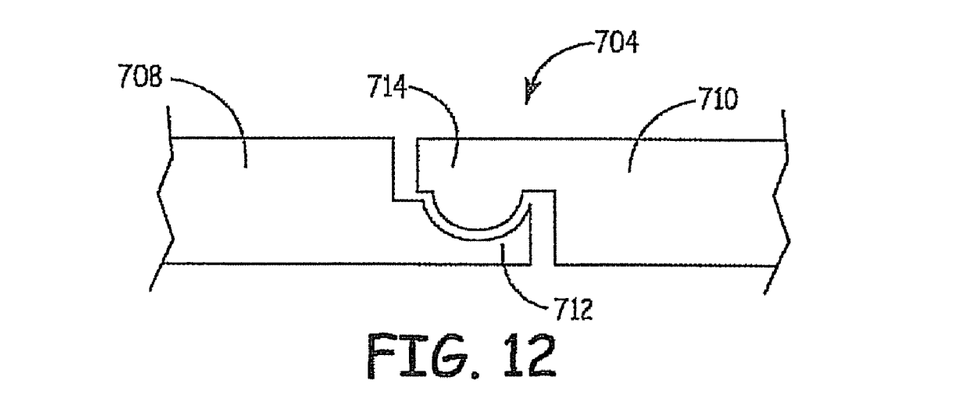
FIG. 12 is a fragmentary side view of an elongated element of a seventh embodiment of a medical device with interlocking segments depicting a first segment coupled to a second segment via a mechanical interface with curved interlocking features.
Figure 13:
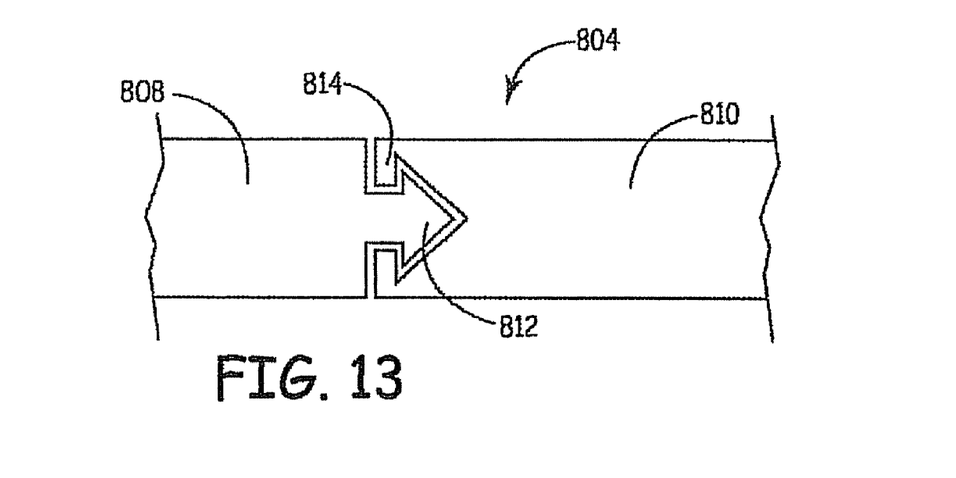
FIG. 13 is a fragmentary side view of an elongated element of an eighth embodiment of a medical device with interlocking segments depicting a first segment coupled to a second segment via a mechanical interface with a cut out arrow format.

Examples of additional exemplary shapes permitting a first segment of an elongated element to be mechanically mated to a second segment of an elongated element with first and second interfaces, respectively, are depicted in FIGS. 11-13. These examples, and other shapes and configurations recognized by those of ordinary skill in the art, can also be used be used where the locking element comprises shaped interfaces, such as those depicted in FIGS. 5, 8-9, and 14.

Referring to FIG. 11, corewire 604 of other embodiments can comprise first segment 608 mechanically coupled to second segment 610. In these embodiments, first segment 608 can comprise angled key portion 612 which can mate with corresponding angled lock portion 614 formed into second segment 610 to mechanically mate first segment 608 to second segment 610.

Referring to FIG. 12, corewire 704 of other embodiments can comprise first segment 708 mechanically coupled to second segment 710. In these embodiments, first segment 708 can comprise rounded key portion 712 which can mate with corresponding rounded lock portion 714 formed into second segment 710 to mechanically mate first segment 708 to second segment 710.

Referring to FIG. 13, corewire 804 of other embodiments can comprise first segment 808 mechanically coupled to second segment 810. In these embodiments, first segment 808 can comprise protruding key portion 812 which can mate with corresponding recessed lock portion 814 formed into second segment 810 to mechanically mate first segment 808 to second segment 810.

Figure 14:
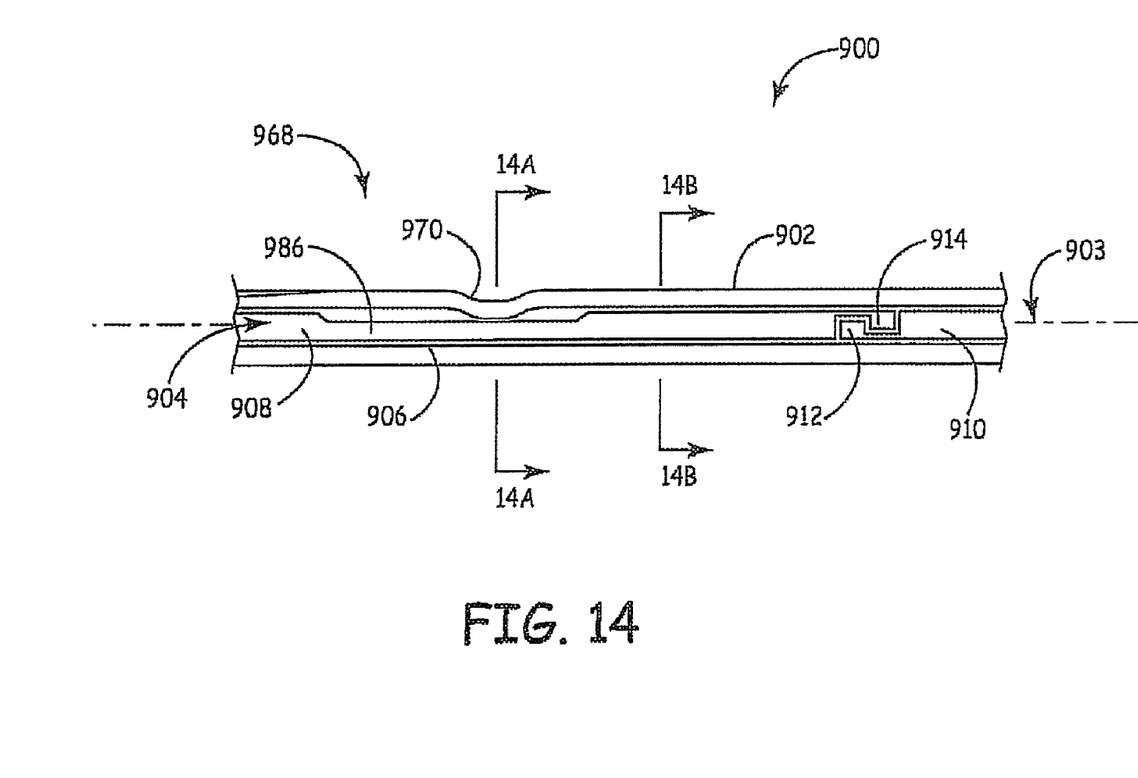
FIG. 14 is a fragmentary perspective view of a medical device of a ninth embodiment of a medical device with interlocking segments depicting a torque coupler connecting a segmented corewire with an overtube.
Figures 14A, 14B:
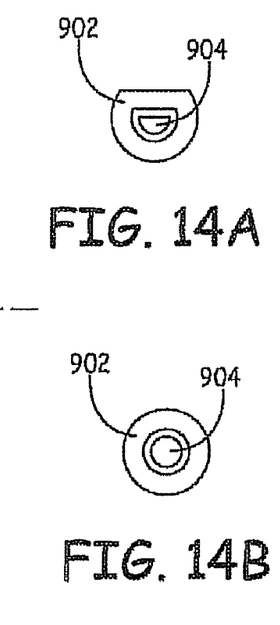
FIG. 14A is a cross-sectional view of the medical device of FIG. 14, the cross-section taken along line 14A-14A of FIG. 14.
FIG. 14B is a cross-sectional view of the medical device of FIG. 14, the cross-section taken along line 14B-14B of FIG. 14.

Referring to FIGS. 14, 14A, and 14B, the medical device can also comprise a torque coupler to enable torque coupling between the corewire and the tube such that torque applied to one of the elements at a proximal end can be more effectively transferred to a distal end. Referring to FIG. 14, a medical device 900 is depicted comprising a tube 902 and a corewire 904 extending into the interior of tube 902. Generally, tube 902 has a major axis 903 along an elongated dimension of the tube relative to a minor axis lying in a minor plane, and a bore 906 that runs substantially parallel to the major axis 903. As depicted in FIG. 27, the corewire 904 can be selectively and slidably positioned within bore 906. Corewire 904 is elongated also along axis 903. Corewire 904 can comprise first segment 908 mechanically coupled to second segment 910. In some embodiments, first segment 908 can comprise key portion 912 which can mate with corresponding lock portion 914 formed into second segment 910 to mechanically mate first segment 908 to second segment 910.

Medical device 900 can also include a torque coupler 968 to provide torque coupling between the corewire 904 and the tube 902 and may also restrict of eliminate relative longitudinal motion of the corewire 904 relative to the tube 902 and along axis 903. Referring to FIGS. 14A and 14B, tube 902 comprises notch 970 that forms a portion of the torque coupler 968. Referring to FIGS. 14 and 14A, corewire 904 has a flattened key portion 986 on the first segment 908 that also forms a portion of torque coupler 968. When medical device 900 is assembled, notch 970 fits within flattened key portion 986 to form torque coupler 968. Once torque coupler 968 is fully formed, the longitudinal motion of corewire 904 along axis 903 is limited within tube 902 such that sufficient movement of corewire 904 relative to hypotube 902 to control and manipulate medical device 900 while limiting complications due to unwanted movement of corewire 904. Also, the communication between the notch 902 and flattened portion 904 enables enable torque coupling between the corewire 904 and the tube 902 such that torque applied to one of the elements at a proximal end can be more effectively transferred to a distal end. Alternative embodiment of torque couples are described, for example, in copending U.S. patent application Ser. No. 10/979,439 to Galdonik et al., and Ser. No. 11/072,001 to Galdonik et al., both entitled "Steerable Device Having a Corewire Within a Tube and Combination with a Functional Medical Component," both of which are incorporated herein by reference.

In general, elongated structures and the locking structures as described herein can be formed from one or more of various materials, such as polymers, metals and combinations thereof. The tube and corewire might or might not be formed from the same material. Suitable materials are generally bio compatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as ELGILOY® a cobalt-chromium-nickel alloy, MP35N, a nickel-cobalt-chromium-molybdenum alloy, NITINOL®, a nickel-titanium alloy, and combinations thereof Shape memory alloys such as, for example, NITINOL® or the like can be particularly useful in some applications because the material is resistant to bending so that a kink would not form to inhibit the sliding of the structure.

Suitable polymers that can be used in the various embodiments include, for example, synthetic polymers as well as purified biological polymers and combinations thereof. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, other copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone, other copolymers and mixtures thereof.

Functional Medical Components for use with Integrated Guiding Device

In general, a functional medical component can be combined with the integrated guiding devices described herein. This can be particularly useful for an actuatable medical structure that can be actuated through the relative longitudinal motion of the corewire and the tube. Generally, this actuatable structure is located at or near the distal end of the integrated guiding device with corresponding actuation by the user at the proximal end of the device. For example, small grippers or fastener applicators can be placed at the end of the device. Suitable designs for a gripper and/or a fastener applicator that can be actuated with the relative motion of the corewire and the tube are described, for example, in U.S. Pat. No. 6,165, 183 to Kuehn et al., entitled "Mitral And Tricuspid Valve Repair," incorporated herein by reference.

In addition, the functional medical component can be an embolism protection structure. In some embodiments, an embolism protection structure is placed near the distal end of the integrated guiding device. Relative motion of the corewire and the tube can be used to deploy the embolism protection structure from a confined narrow profile configuration for delivery to a deployed configuration at which the embolism protection structure is expanded within the vessel. The actuation, which is generated by the longitudinal motion of the tube relative to the corewire, can release the embolism protection structure from a constrained environments, or can directly drive a reconfiguration of the device into a form that filters the lumen of the vessel. Embolism protection structures of particular interest include, for example, fiber based embolism protection structures as described in co-pending application Ser. No. 10/979,439 to Pokomey et al., entitled "Steerable Device Having a Corewire Within a Tube and Combination with a Functional Medical Component," incorporated herein by reference.

Distribution and Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together.

Various devices described herein can be packaged together in a kit for convenience. The kit can further comprise, for example, labeling with instruction for use and/or warnings, such as information specified for inclusion by the Food and Drug administration. Such labeling can be on the outside of the package and/or on separate paper within the package.

The present invention may be embodied in other specific forms without departing from the spirit of any of the essential attributes thereof. Therefore, the illustrated embodiments should be considered in all respects as illustrative and not restrictive, reference being made to the appended claims rather than to the foregoing description to indicate the scope of the invention.

What is claimed is:

1. A biocompatible medical device comprising:
   a segmented element comprising,
   a first segment having a first shaped interface, and a second segment having a second shaped interface configured to operably couple the first shaped interface of the first segment to form a joined segmented element, wherein the joined segmented element can be decoupled through relative translational perpendicular separation of the segments with respect to a longitudinal axis of the element wherein the segments become non-coaxial along the longitudinal axis, and
   a locking element configured to engage with a sliding motion the joined segmented element to maintain the coupling of the first segment with the second segment by preventing significant relative perpendicular or longitudinal movement of the segments with respect to the longitudinal axis, wherein when engaged, there is no significant gap between the locking element and the joined segmented element.

2. The medical device of claim 1 wherein the segmented element comprises a corewire and the locking element comprises a tube having a bore defined therein, wherein the corewire is configured to be selectively disposed within the bore of the tube to prevent decoupling of the first segment from the second segment.

3. The medical device of claim 1 wherein the segmented element comprises a tube having a bore defined therein and the locking element comprises a corewire configured to be selectively disposed within the bore of the tube to prevent decoupling of the first segment with respect to the second segment.

4. The medical device of claim 1 wherein the locking element comprises a third segment having a third shaped interface and a fourth segment having a fourth shaped interface configured to operably couple the third shaped interface, such that the segmented element prevents decoupling of the third segment with respect to the fourth segment.

5. The medical device of claim 1 wherein the joined segmented element forms a generally cylindrical outer surface in a direction generally parallel with the longitudinal axis.

6. The medical device of claim 5 wherein the generally cylindrical outer surface comprises narrowed profiles along the first and second segments wherein a polymer coating is located within the narrow profile that provides mechanical stability to the joined segmented element.

7. The medical device of claim 1 wherein at least one of the segmented element or locking element is coated with a friction reducing agent to facilitate relative longitudinal motion of the segmented element relative to the locking element.

8. The medical device of claim 1 wherein the first and second segments each independently comprise materials selected from the group consisting of: titanium; cobalt; stainless steel; nickel; iron alloys; cobalt alloys; cobalt-chromium-nickel alloys; nickel-cobalt-chromium-molybdenum alloys; nickel-titanium alloys; and any combinations thereof.

9. The medical device of claim 1 wherein the locking element comprises a material selected from the group consisting of: polyether ether ketones; polyacetals; polyamides; polyurethanes; polytetrafluoroethylene; polyester teraphthalate; polycarbonates; polysulfone; and any combination thereof.

10. The medical device of claim 1 wherein the first and second segments each comprise materials selected from the group consisting of: polyether ether ketones; polyacetals; polyamides; polyurethanes; polytetrafluoroethylene; polyester teraphthalate; polycarbonates; polysulfone; and any combination thereof.

11. The medical device of claim 1 wherein the locking element comprises a material selected from the group consisting of: titanium; cobalt; stainless steel; nickel; iron alloys; cobalt alloys; cobalt-chromium-nickel alloys; nickel-cobalt-chromium-molybdenum alloys; nickel-titanium alloys; and any combinations thereof.

12. The medical device of claim 1 further comprising a functional medical device at or near a distal end of the segmented element.

13. The medical device of claim 12 wherein the functional medical device comprises an embolism protection structure comprising fibers attached to both the first segment and the locking element.

14. The medical device of claim 1 wherein the joined segmented element has a length from about 190 cm to about 300 cm.

15. The medical device of claim 1 wherein the joined segmented element has an outer diameter from about 0.009 inches to about 0.04 inches.

16. A method for using a medical device comprising directing the medical device of claim 1 through appropriate vessels to a desired location within a patient.

17. The method of claim 16 wherein the medical device is inserted into the patient through an incision in the patient's thigh, arm or neck.

18. The method of claim 16 wherein the medical device further comprises an embolism protection device connected to the joined segmented element and the method further comprises deploying the embolism protection structure to a vessel and expanding the embolism protection structure within the vessel.

19. The method of claim 16 further comprising using the device in conjunction with a catheter to position the medical device at the desired location within the patient.

20. A biocompatible medical device comprising
   a segmented element comprising,
   a first segment having a first shaped interface, and a second segment having a second shaped interface configured to operably couple the first shaped interface of the first segment to form a joined segmented element, wherein the joined segmented element cannot be decoupled by movement along a longitudinal axis of the element and is decoupled through movement resulting in the segments being non-coaxial along the longitudinal axis, and wherein the first and second segments are comprised of different materials, and a locking element configured to engage with a sliding motion the joined segmented element to maintain the coupling of the first segment with the second segment by preventing significant relative perpendicular movement of the segments with respect to the longitudinal axis, wherein when engaged, there is no significant gap between the locking element and the joined segmented element, wherein the first and second segments are further operably coupled with a joining composition or with a weld.

21. The medical device of claim 20 wherein the first segment and the second segment are welded.

22. A method of using a biocompatible medical device comprising a locking element and a segmented element having first and second coupled segments operably inseparable along a longitudinal axis, the method comprising:

slidably engaging the locking element with the segmented element to prevent significant relative perpendicular movement of the segments with respect to the longitudinal axis, wherein the first coupled segment and the second coupled segment decouple through relative perpendicular separation of the segments with respect to the longitudinal axis in which the segments become non-coaxial along the longitudinal axis and wherein the first and second segments are comprised of different materials, wherein when engaged, there is no significant gap between the locking element and the segmented element.

23. The method of claim 22 further comprising slidably disengaging the locking and the segmented elements and decoupling the first and second segments.

* * * * *